United States Patent [19]

Fitz-Patrick

[11] Patent Number: 5,135,305
[45] Date of Patent: Aug. 4, 1992

[54] SPECTROANALYTICAL SYSTEM

[75] Inventor: Bruce C. Fitz-Patrick, Franklin, Mass.

[73] Assignee: Thermo Jarrell Ash Corporation, Waltham, Mass.

[21] Appl. No.: 662,931

[22] Filed: Mar. 1, 1991

[51] Int. Cl.⁵ .................... G01J 3/10; G01J 3/42
[52] U.S. Cl. ...................... 356/311; 356/312; 356/315; 356/325; 356/328; 187/24; 187/35
[58] Field of Search .............. 356/311, 312, 315, 316, 356/319, 326, 328, 323, 325; 187/8.71, 17, 18, 24, 25, 35; 269/58–61; 49/28

[56] References Cited

U.S. PATENT DOCUMENTS

| 3,472,488 | 10/1969 | Naughton | 187/18 |
| 3,532,429 | 10/1970 | Hughes et al. | |
| 3,586,441 | 6/1971 | Smith et al. | |
| 3,600,571 | 8/1971 | Chisholm et al. | |
| 3,625,328 | 12/1971 | Carli | 49/28 |
| 4,469,441 | 9/1984 | Bernier et al. | 356/316 |
| 4,867,562 | 9/1989 | Oishi et al. | 356/312 |
| 4,875,555 | 10/1989 | Johansson et al. | 187/25 |
| 4,930,892 | 6/1990 | Hadbawnik et al. | 356/328 |
| 4,969,793 | 11/1990 | Pawl | 187/18 |
| 5,035,505 | 7/1991 | Tsukada et al. | 356/312 |

FOREIGN PATENT DOCUMENTS 750809   1/1967   Canada ........................ 187/18

Primary Examiner—F. L. Evans
Attorney, Agent, or Firm—Fish & Richardson

[57] ABSTRACT

A positioning mechanism support structure mounted for movement between first and second predetermined positions in a spectroanalytical system includes relative to a reference member by a plurality of stabilizing coupling assemblies, and drive structure for producing motion of the support structure relative to the reference structure between first and second stop structures that define the first and second predetermined positions, respectively. Interlock structure responds to the drive force generated by the drive structure and de-energizes the drive structure in response to the drive force applied to that support structure exceeding a predetermined threshold value.

11 Claims, 6 Drawing Sheets

5,135,305

SPECTROANALYTICAL SYSTEM

BACKGROUND AND SUMMARY OF THE INVENTION

This invention relates to positioning systems, and more particularly to positioning systems useful in optical systems such as spectroanalytical systems of the absorption type.

Frequently, it is desirable to provide rapid, reliable and repeatable shifting of optical components such as radiation sources into and out of a precise analytical position.

In accordance with one aspect of the invention, there is provided a positioning mechanism for moving support structure between first and second predetermined positions. The support structure is mounted for movement relative to a reference member by a plurality of stabilizing coupling assemblies, and drive structure produces motion of the support structure relative to the reference structure between first and second stop structures that define the first and second predetermined positions, respectively. Interlock structure responds to the drive force generated by the drive structure and de-energizes the drive structure in response to the drive force applied to that support structure exceeding a predetermined threshold value.

In preferred embodiments, a plurality of groups of radiation sources are mounted at a sequence of levels or positions on the support structure and level selection structure includes stop structure which defines an analysis position corresponding to a particular group of radiation sources.

In a particular embodiment, the coupling assemblies provide stable support structure guidance and include counter-gravity biasing arrangements that minimize the load of the support structure on the drive structure.

In a particular embodiment, the drive structure includes a drive motor and a threaded drive shaft that are coupled together by a elongated flexible force transmitting drive member. An idler member is biased to apply tension to the force transmitting member. A controller energizes the drive motor in forward or reverse direction through a bridge circuit and concurrently releases a brake. The interlock structure responds to increased tension (of less than ten pounds) in the flexible force transmitting drive member and opens an interlock switch in the circuit to concurrently de-energize the drive motor and apply the brake to hold the drive shaft in fixed position.

In that embodiment, the positioning system is incorporated in a spectroanalytical system that includes an optical system with a bank of cassettes containing up to eight hollow cathode lamps in two arrays of four each in vertically spaced planes on a platform support structure. A selected array of hollow cathode lamps is accurately positioned by the positioning system in an analytical plane, and a particular hollow cathode lamp is selected by a galvanometer driven mirror system. Optically coupled to the hollow cathode lamp array is an analysis region for thermally exciting a sample material to be analyzed and a high-resolution monochromator with a galvanometer driven grating for line selection, a dual beam optical pathway, and a high sensitivity photomultiplier detector.

The galvanometer drives for wavelength and lamp selection are fast (a wavelength range of more than five hundred nanometers in less than one hundred milliseconds) and of high resolution (0.08 to two nanometers). The analysis system is like an inexpensive plasma spectrometer with extraordinary sensitivity and can be configured to determine large number of elements is a single unattended run with each element being determined at PPB levels.

Other features and advantages of the invention will be seen as the following description of a particular embodiment progresses, in conjunction with the drawings, in which.

DESCRIPTION OF PARTICULAR EMBODIMENT

Figure 1:
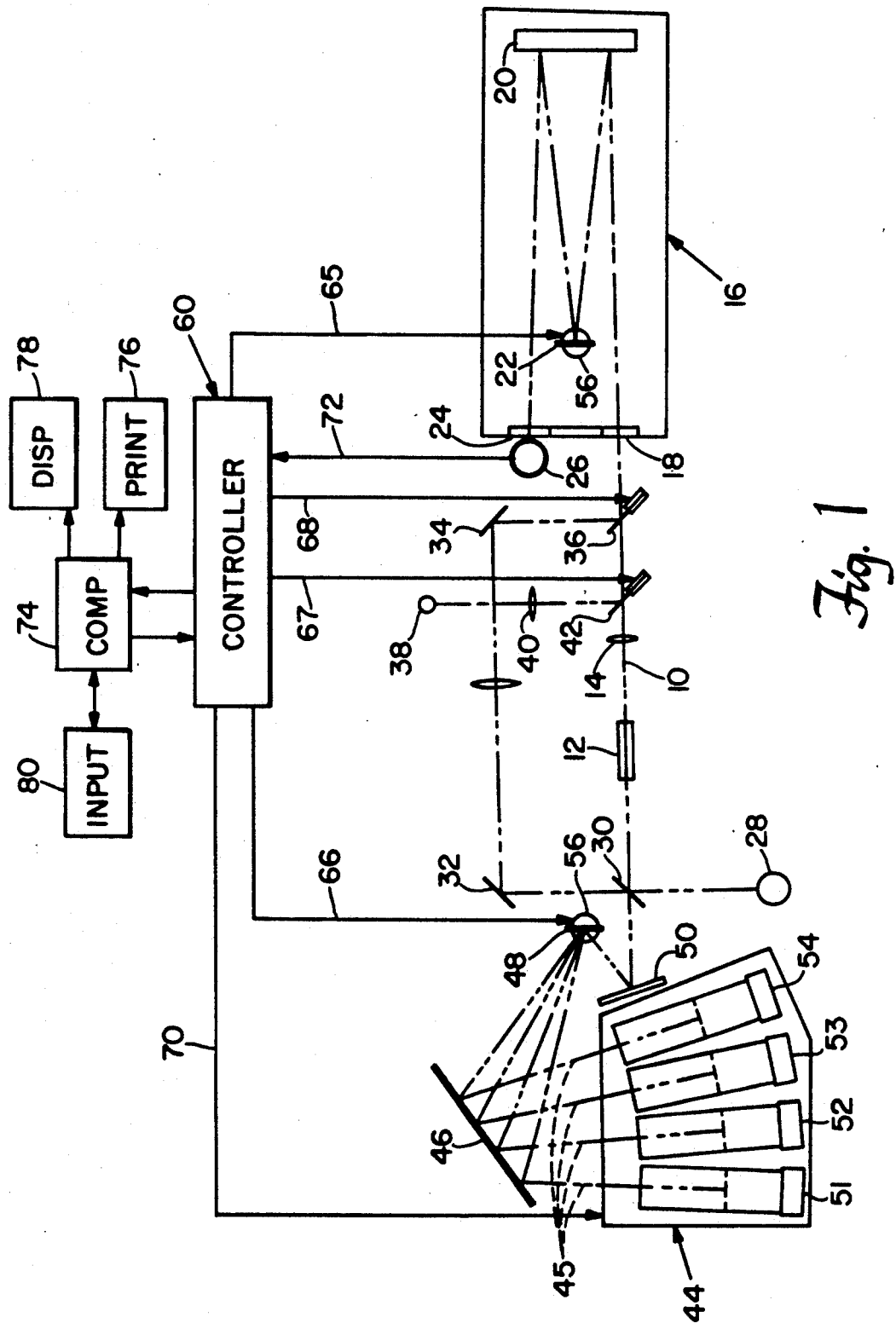
FIG. 1 is a diagram of a spectroanalytical system in accordance with the invention.

With reference to FIG. 1, the atomic absorption system there shown includes analysis beam path 10 on which is disposed an analysis region that includes thermal excitation structure 12 such as a flame atomizer or furnace, lens 14, and one third meter Ebert monochromator 16 that has entrance slit defining structure 18, mirror 20, 800 grooves per millimeter dispersion grating 22, exit aperture defining structure 24 and photomultiplier tube sensor 26. Slit structures 18 and 24 may be of the type shown in U.S. Pat. No. 3,508,813, the disclosure of which is expressly incorporated herein by reference. The system is capable of flame atomic emission spectroscopy as well as atomic absorption analysis, and is equipped for excitation of elements by either flame or furnace; the flame atomizer can be furnished with burners for both air/acetylene and nitrous oxide/acetylene flames.

Optional supplemental elements include a reference beam system that includes deuterium arc source 28, mirrors 30, 32, 34 and retractable mirror 36; and a wavelength calibration system that includes mercury source 38, lens 40 and retractable mirror 42.

Figure 4:
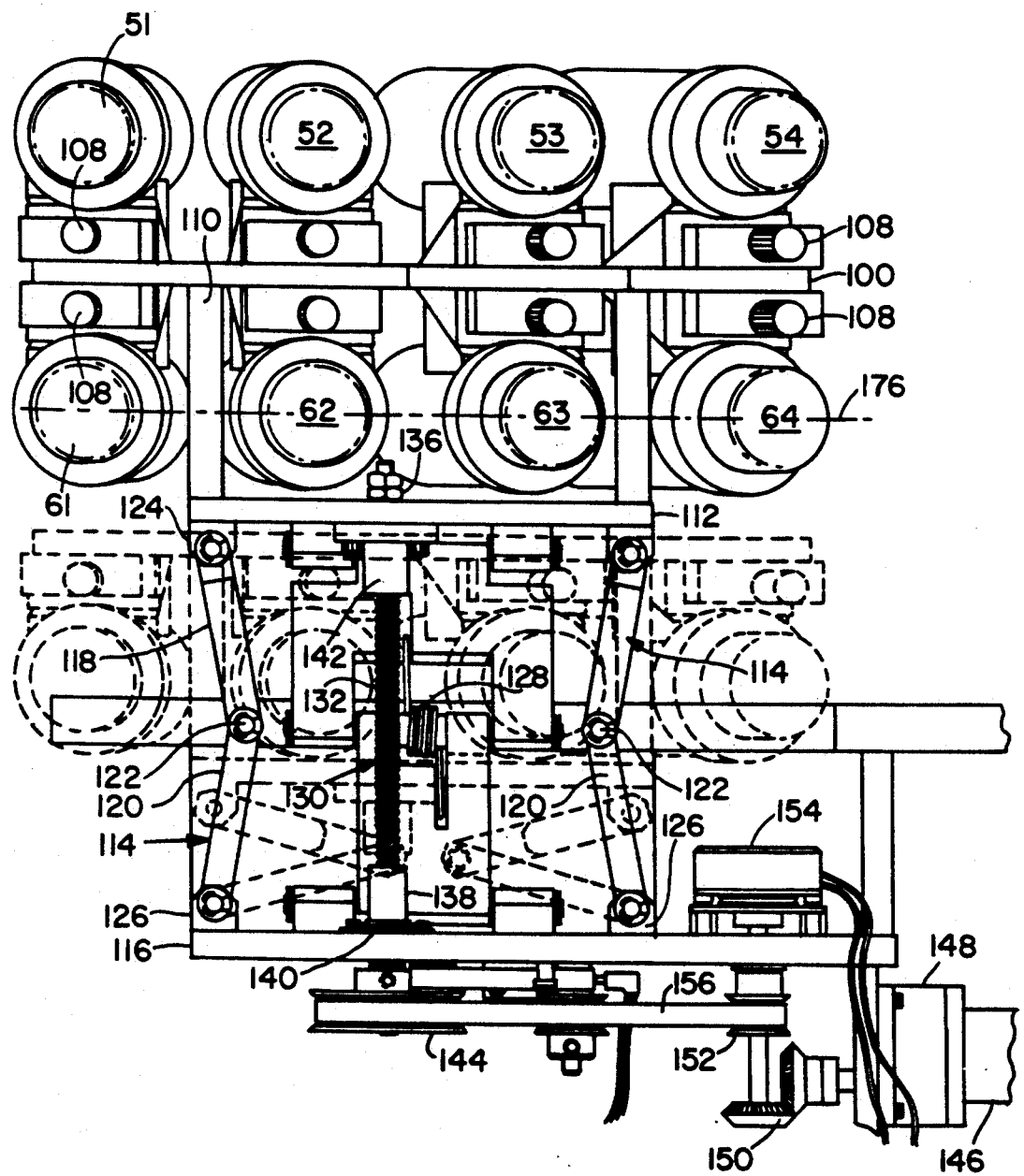
FIG. 4 is a front elevational view of the source assembly shown in FIG. 3.

Two arrays of hollow cathode lamps 51-54, 61-64 (FIG. 4) are supported on elevator assembly 44 and either array may be positioned by the elevator assembly 44 so that the beams 45 of its lamps are directed at planar reflector 46, for reflection to selector mirror 48 and toroidal mirror 50 to direct radiation along beam path 10 through the analysis region to monochromator 16. Hollow cathode lamps 51-54 may be arsenic, selenium, thallium and lead, for example; and the hollow cathode lamps 61-64 may be of other types, some or all of which may be multiple-element lamps. Grating 22 and selector mirror 48 are individually mounted on support and drive assemblies 56 that respond to signals, preferably digital signals of at least sixteen binary digits, from controller 60 over lines 65, 66, respectively. Controller 60 also generates signals over lines 67, 68 to control retractable mirrors 36, 42; over lines 70 to control source positioning elevator assembly 44; and receives signals over line 72 from sensor 26 for application to computer 74 for data processing and application of outputs to printer 76 and display 78, and control signals from input keyboard 80. Thus, the entire optical system—including the elevator assembly 44 that positions the lamps 51-54 and 61-64, the galvanometer drives 56, the retractable mirrors 36, 42, and the parameter settings on the photomultiplier 26—is under microprocessor control. The analyzer can run unattended, and in such operation, standards and samples can be rerun, different groups of elements can be analyzed, and the sample volume can be varied.

Figure 2:
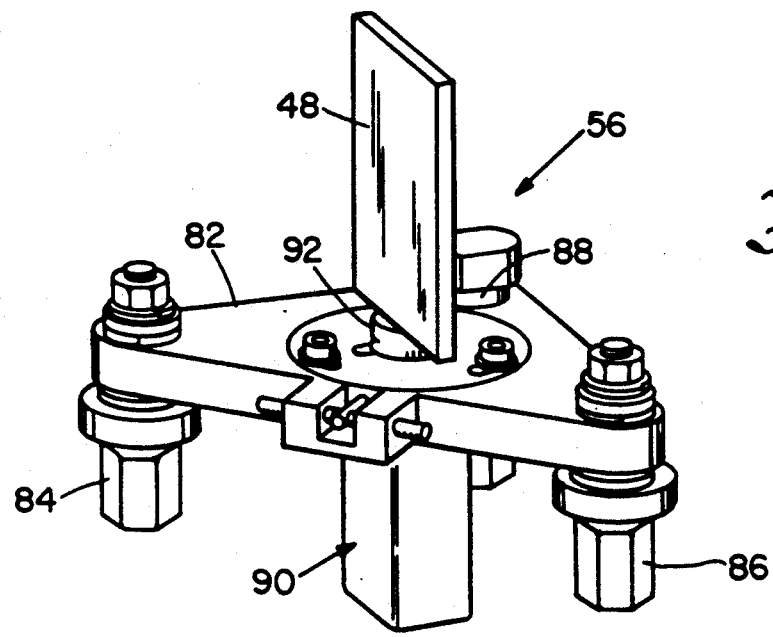
FIG. 2 is a perspective view of a source selector mirror assembly employed in the system shown in FIG. 1.
Figure 3:
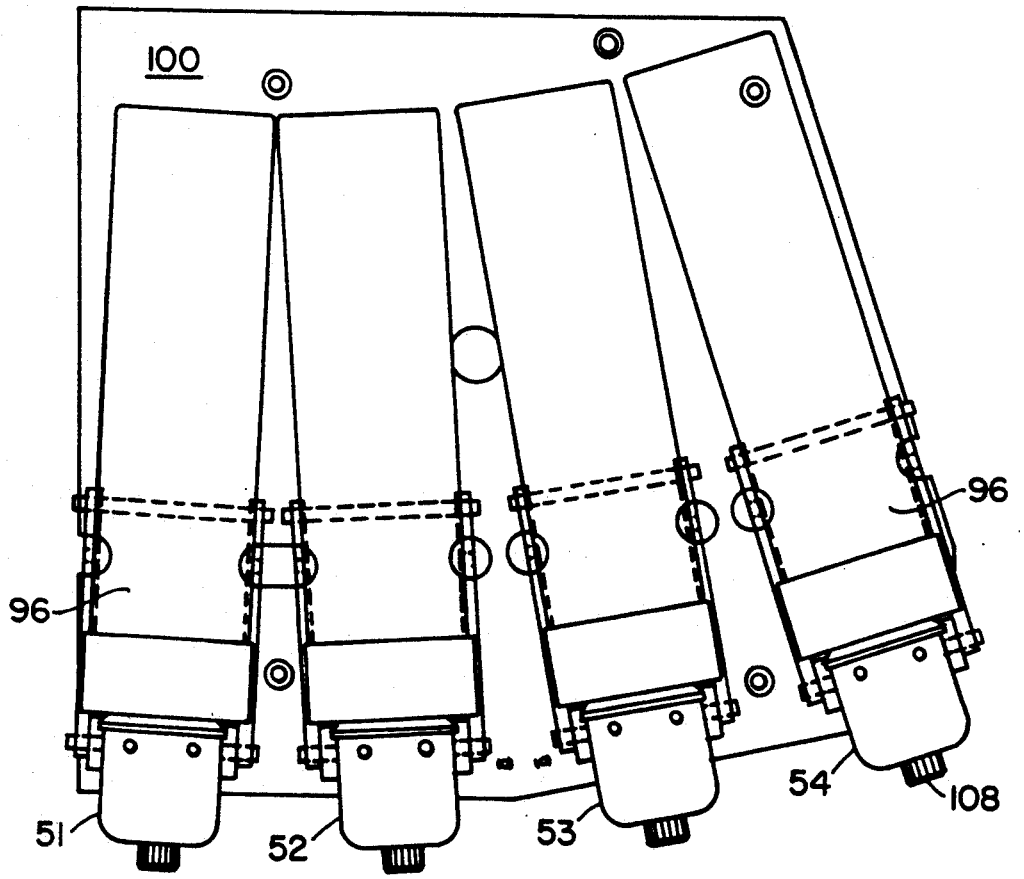
FIG. 3 is a top view of a source assembly employed in the system of FIG. 1.
Figure 5:
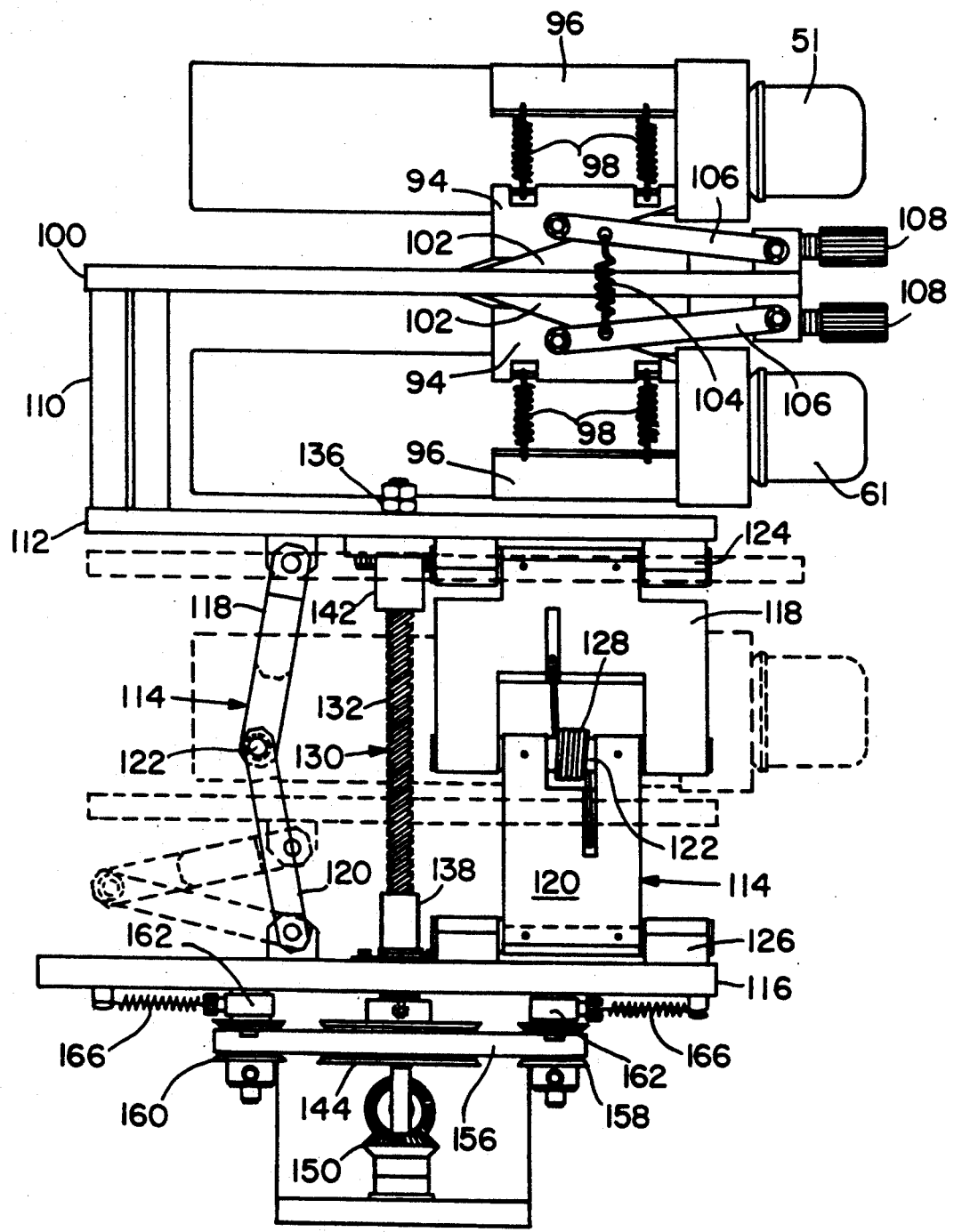
FIG. 5 is a side elevational view of the source assembly shown in FIG. 3.
Figure 6:
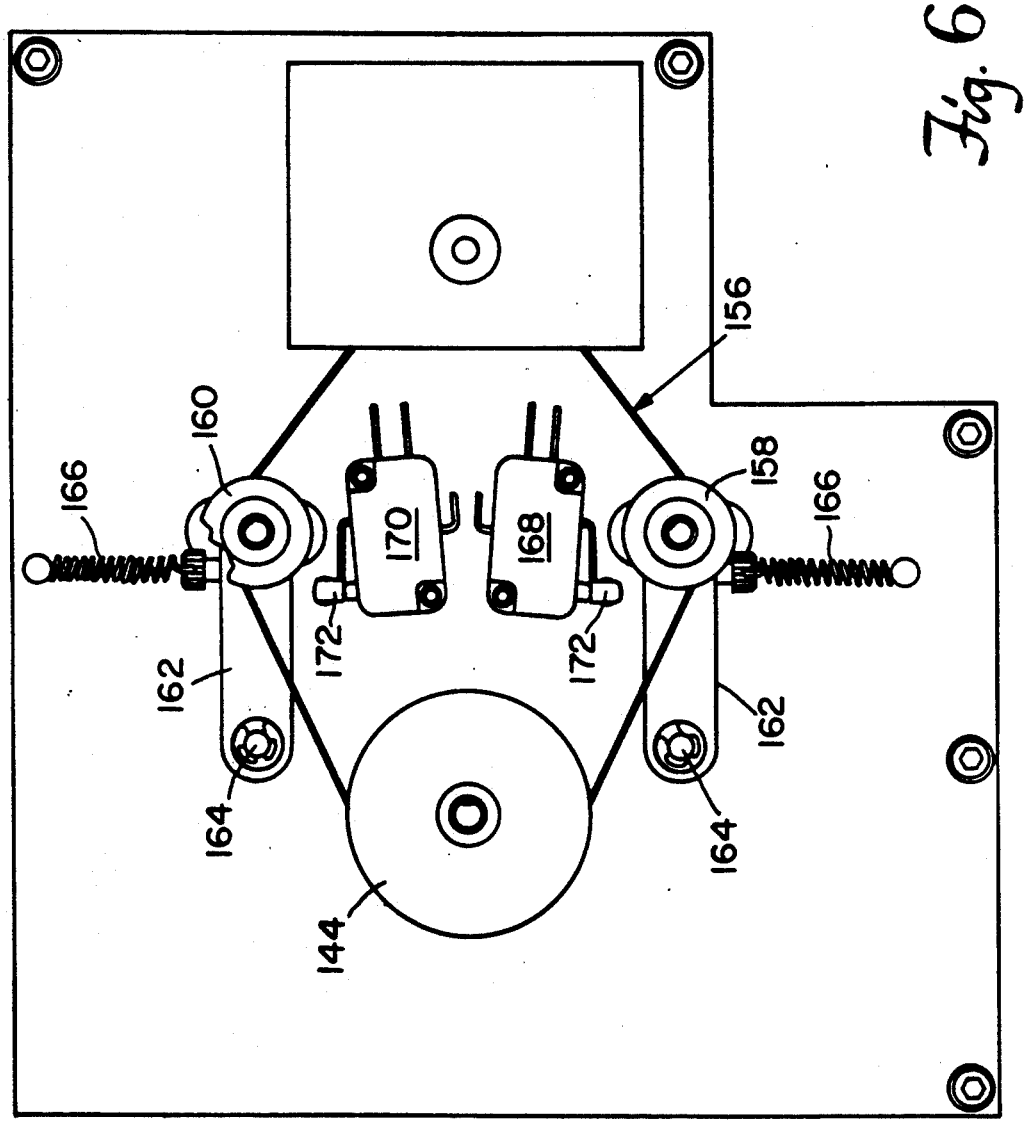
FIG. 6 is a bottom plan view of the source assembly shown in FIGS. 3-5 showing aspects of the drive system.

Each drive assembly 56 is of the type shown in FIG. 2, and includes support plate 82 of triangular configuration that is mounted on upstanding posts 84, 86, 88 that provide two mutually independent tilt adjustments. Carried on plate 82 is limited rotation motor 90 which includes upwardly projecting shaft 92 to which the grating 22 or the mirror 48, respectively, is clamped. Each transducer 90 rotates its optical component over an angle of plus or minus 8 ½ degrees in response to digital input signals. Further details of drive assembly 56 may be had with reference to Bernier U.S. Pat. No. 4,469,441, the disclosure of which is expressly incorporated herein by reference. During initial installation, monochromiator 16 may be calibrated from the mercury source 38, the hollow cathode lamps 51-54 and 61-64 aligned vertically, and a peak reading for each source identified and stored in the memory of computer 74. Further aspects of elevator assembly 44 and the arrays of the hollow cathode tubes 51-54 and 61-64 may be seen with reference to FIGS. 3-5. As is shown in FIG. 5, each hollow cathode tube is secured on seat 94 by clamp plate 96 and biasing springs 98. Mounted on aluminum plate 100 are ramp members 102, and seats 94 are biased against their respective ramp members by springs 104 that are connected to arms 106 which are connected to seats 94 and are also connected to adjustment mechanisms 108 for varying the relative vertical positionings of the several hollow cathode lamps 51-54 and 61-64.

Platform 100 of the elevator assembly 44 is supported by posts 110 on plate 112 that in turn is supported by scissor arm assemblies 114 from fixed base 116. Each scissor arm assembly 114 includes arm members 118, 120 that are pivoted together at 122 and secured by brackets 124 to platform 112 and brackets 126 to base 116. Coil spring 128 of each assembly 114 provides a biasing force that acts between arms 118 and 120 to oppose the force of gravity.

Also coupled between platform 112 and base 116 is drive screw assembly 130 that includes 0.6 centimeter diameter Teflon impregnated hard anodized aluminum drive shaft 132 that has thread 134 with a lead of about 1.2 centimeters and about six threads per centimeter. The upper end of shaft 132 is of reduced diameter and carries upper stop 136. Brass lower stop sleeve 138 is at the base of shaft 132 just above self-aligning bearing 140. Threadedly carried on shaft 132 is acetal (Delrin, nut 142. Shaft 132 extends through self-aligning bearing 140 in base 116 and is coupled to drive pulley 144.

Figure 7:
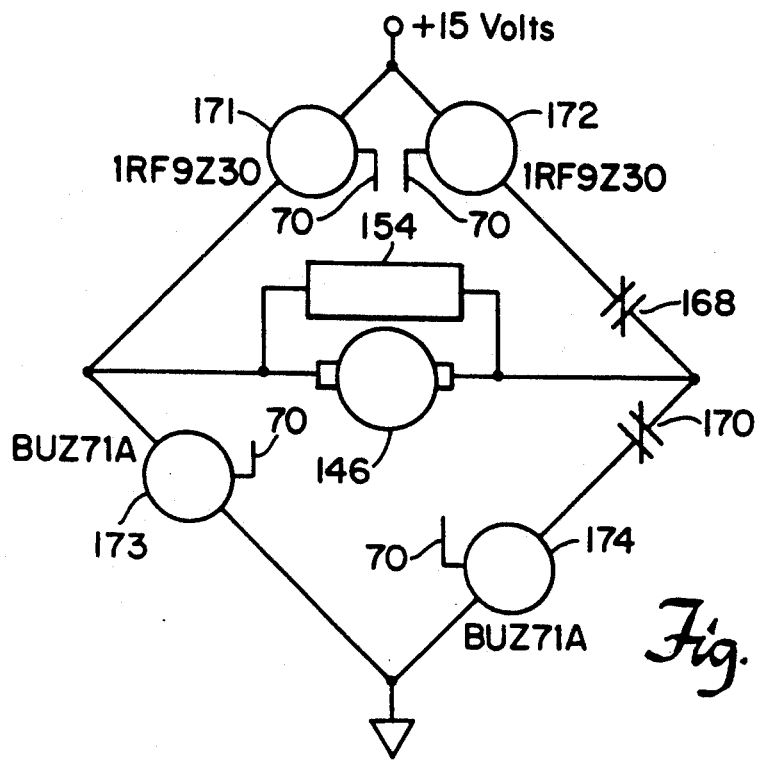
FIG. 7 is a diagram of circuitry employed in the drive system shown in FIGS. 6.

Further details of the elevator drive system may be seen with reference to FIGS. 4-7. That drive system includes 12 volt DC motor 146 with a 60:1 gear reducer 148 that is connected through gears 150 to drive pulley 152. Coupled to drive pulley 152 is brake 154. 0.6 centimeter wide timing belt 156 is trained over idler pulleys 158, 160, each of which is carried on actuator link 162 which in turn is mounted for rotation about pivot 164 and biased outwardly by spring 166. Lever type switches 168, 170 each includes an actuator 172 that is aligned with the adjacent actuator link 162. Switches 168, 170 are interconnected in motor and brake bridge circuit as shown in FIG. 7. That circuit includes controllers 171-174 that receive control signals from controller 60 over lines 70. Motor 146 is energized in the clock-wise direction by closing controllers 171 and 174; and in the reverse direction by closing controllers 172 and 173; and brake 154 is concurrently energized and held in its open (released) state. If the load on drive screw 132 increases, due to nut 142 reaching either the upper stop 136 or the lower stop 138 (or if the movement of plate 112 encounters modest resistance (of about three pounds) due, for example, to an obstruction), tension on the drive belt 156 increases in the drive direction, and the corresponding idler pulley 160 is pivoted against biasing force of its spring 166 to actuate the corresponding interlock switch 168 or 170 and de-energize motor 146 and release brake 154 to hold shaft 132 in position.

The overall travel of the hollow cathode tube elevator plate 100 (from stop 136 to stop 138) is about six centimeters and requires about six seconds. In the upper position (with nut 142 abutting upper stop 136), the lower bank of hollow cathode tubes 61-64 is disposed in the optical plane 176 of beam path 10. In the lower position (with nut 142 abutting lower stop 138), the upper bank of hollow cathode tubes 51-54 are disposed in the optical plane 176.

In this travel, motor 146 is energized in the clockwise direction to move nut 142 downwardly by closing of controllers 171 and 174 in response to a signal on line 70. When nut 142 contacts stop 138, the tension in that portion of drive belt 156 trained over idler pulley 160 increases and pivots link 162 against the force of spring 166 against actuator 172 of switch 170 to open that switch and de-energize motor 146 and apply brake 154 to hold plate 100 in the lower (dotted) position with the upper bank of hollow cathode tubes 51-54 disposed in optical plane 176.

In that position, a spectrochemical analysis is initiated by aspirating the sample to be analyzed into the flame of the flame atomizer 12. Mirror 48 is positioned by its drive 56 to pass radiation from a selected one of the bank of hollow cathode tubes 51-54 through the analysis region 12 and entrance slit 18 of monochromator 16. Concurrently, grating 22 is positioned by signals from controller 60 over line 65 to select the corresponding wavelength at the exit slit 24 for sensing by photomultiplier tube 26. The drive voltage range is plus or minus 5 volts and the digital input signal excursion is plus or minus 131072 steps. The desired grating position determines the binary member input and that value is used by controller 60 in the grating equation to determine the correct binary input required to produce the grating angle for the desired wavelength. The drive transducers 56 for mirror 48 and grating 22 are repeatedly adjusted during an analysis of the sample. Due to the speed of the galvanometer driven movement of the mirror 48 and grating 22, a sequence of beams from the four hollow cathode tubes is passed through the aspirated sample in the flame of the atomizer 12 many times during the course of one flame aspiration cycle.

The galvanometer drives for wavelength and lamp selection are fast (from 185 nanometers wavelength to 900 nanometers wavelength in twenty milliseconds) and wavelength selection has high resolution in the range of 0.08 to two nanometers. Each sample is presented in repetitive succession with beams from four hollow cathode lamps. Because of the speed of the galvanometer-driven mirror and grating drives, the sample is presented with each beam many times during the course of one flame aspiration or single atomization cycle.

Figure 8:
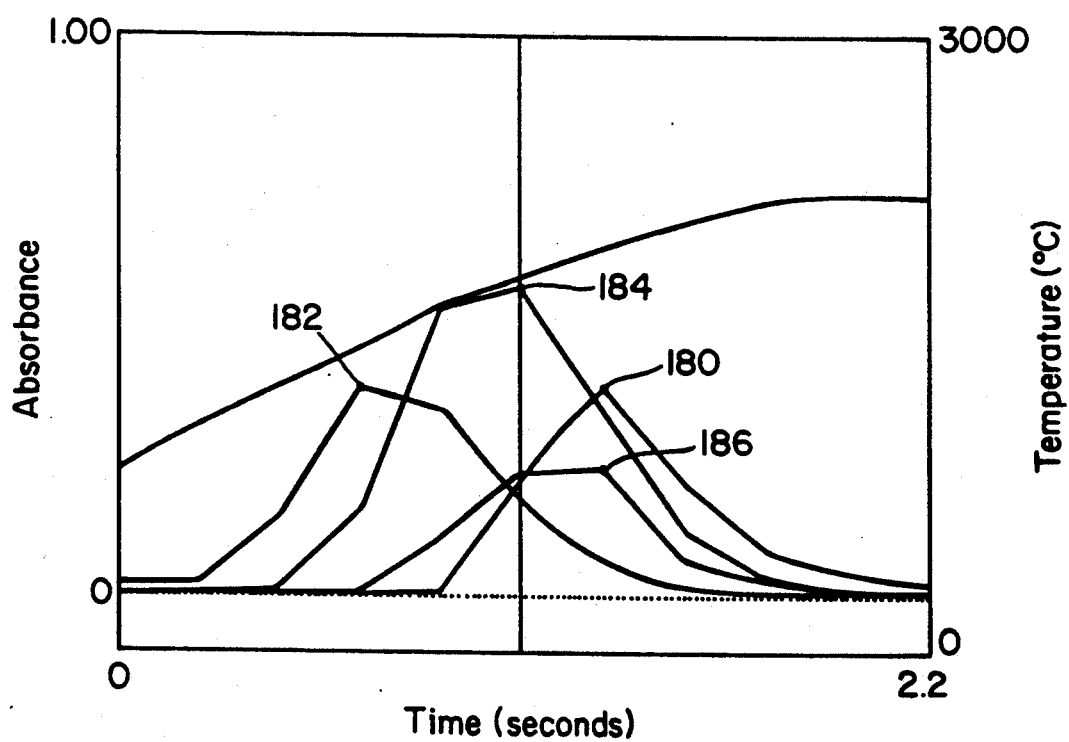
FIG. 8 is a graph of a multi-element measurement made with the system shown in FIG. 1.

A graph of a typical sample analysis (analysis of water with a furnace atomizer for arsenic, selenium, lead and thallium) obtained with the analyzer system of the invention, utilizing one of two four-lamp arrays, is shown in FIG. 8. That graph shows an arsenic peak 180 of 0.200 absorbance units, a selenium peak 182 of 0.221 absorbance units; a lead peak 184 of 0.557 absorbance units; and a thallium peak 186 of 0.169 absorbance units. The analysis duration was about 2.2 seconds, and the lead peak 184 occurred at about 1.1 seconds into the analysis cycle and at a temperature of 1829° C.

While a particular embodiment of the invention has been shown and described, various modifications will be apparent to those skilled in the art, and therefore, it is not intended that the invention be limited to the disclosed embodiment, or to details thereof, and departures may be made therefrom within the spirit and scope of the invention.

What is claimed is:

1. A positioning system for moving support structure between first and second predetermined positions comprising a reference member,
   mounting structure including a plurality of stabilizing coupling assemblies secured to said reference member,
   support structure coupled to said mounting structure for movement relative to said reference member,
   drive structure for producing motion of said support structure relative to said reference structure between first and second predetermined positions,
   interlock structure responsive to the drive force generated by said drive structure for de-energizing said drive structure in response to the drive force applied to said support structure exceeding a predetermined threshold value,
   a plurality of groups of radiation sources mounted at a sequence of levels on said support structure, and
   level selection structure including stop structure for stopping the movement of a particular one of said groups of radiation sources at an analysis position.

2. A positioning system for moving support structure between first and second predetermined positions comprising a reference member,
   mounting structure including a plurality of stabilizing coupling assemblies secured to said reference member,
   said coupling assemblies providing stable guidance for said support structure and including countergravity biasing arrangements that minimize the load of said support structure on said drive structure,
   support structure coupled to said mounting structure for movement relative to said reference member,
   drive structure for producing motion of said support structure relative to said reference structure between first and second predetermined positions, and
   interlock structure responsive to the drive force generated by said drive structure for de-energizing said drive structure in response to the drive force applied to support structure exceeding a predetermined threshold value.

3. A positioning system for moving support structure between first and second predetermined positions comprising a reference member,
   mounting structure including a plurality of stabilizing coupling assemblies secured to said reference member,
   support structure coupled to said mounting structure for movement relative to said reference member,
   drive structure for producing motion of said support structure relative to said reference structure between first and second predetermined positions,
   said drive structure including a drive motor, a threaded drive shaft coupled to said drive motor by a elongated flexible force transmitting drive member, and a nut member mounted on said threaded drive shaft and coupled to said support structure, and
   interlock structure responsive to the drive force generated by said drive structure for de-energizing said drive structure in response to the drive force applied to said support structure exceeding a predetermined threshold value.

4. The system of claim 3 wherein said interlock structure further includes an idler member biased to apply tension to said force transmitting member.

5. The system of claim 3 wherein said drive structure includes a bridge circuit in which an interlock switch, a brake and said drive motor are connected, and further including a controller for energizing said drive motor through said bridge circuit and concurrently releasing said brake, and said interlock structure is responsive to increased tension in said flexible force transmitting drive member for opening said interlock switch in said bridge circuit to concurrently de-energize said drive motor and apply that brake to hold said drive shaft in fixed position.

6. A spectroanalytical system comprising support structure,
   an optical system with two arrays of radiation sources mounted in vertically spaced planes on said support structure,
   a positioning system for moving said support structure between first and second predetermined positions comprising
   a reference member,
   mounting structure including a plurality of stabilizing coupling assemblies secured to said reference member,
   said support structure being coupled to said mounting structure for movement relative to said reference member,
   drive structure for producing motion of said support structure relative to said reference structure between first and second predetermined positions, and
   interlock structure responsive to the drive force generated by said drive structure for de-energizing said drive structure in response to the drive force applied to said support structure exceeding a predetermined threshold value,
   said positioning system being adapted to selectively and accurately position each said array in an analytical plane, a galvanometer driven mirror system for selecting one of said radiation sources, an analysis region for thermally exciting a sample material to be analyzed optically coupled to said mirror system, a high-resolution monochromator with a galvanometer driven grating for line selection, a radiation sensor optically coupled to said monochromator, and a controller for coordinately operating said drive structure, said mirror and grating, and said radiation sensor for analysis of thermally energized sample material in said sample region.

7. The system of claim 6 wherein said coupling assemblies provide stable guidance for said support structure and include counter-gravity biasing arrangements that minimize the load of said support structure on said drive structure.

8. The system of claim 7 wherein each said coupling assembly includes a scissor arm assembly with a pair of arm members that are pivoted together and secured between said reference member and said support structure, and coil spring for providing a biasing force that acts between arm members to oppose the force of gravity.

9. The system of claim 6 wherein said drive structure includes a drive motor, a threaded drive shaft coupled to said drive motor by a elongated flexible force transmitting drive member, and a nut member mounted on said threaded drive shaft and coupled to said support structure.

10. The system of claim 9 wherein said interlock structure further includes an idler member biased to apply tension to said force transmitting member.

11. The system of claim 10 wherein said drive structure includes a bridge circuit in which an interlock switch, a brake and said drive motor are connected, and further including a controller for energizing said drive motor in the forward or reverse direction through said bridge circuit and concurrently releasing said brake, and said interlock structure is responsive to a tension force of less than ten pounds in said flexible force transmitting drive member for opening said interlock switch in said bridge circuit to concurrently de-energize said drive motor and apply said brake to hold said drive shaft in fixed position.

* * * * *